United States Patent [19]

Vanlerberghe et al.

[11] Patent Number: 4,532,125
[45] Date of Patent: Jul. 30, 1985

[54] NEW SURFACE-ACTIVE STATISTICAL OLIGOMERS, A PROCESS FOR THEIR PREPARATION AND COMPOSITIONS IN WHICH THEY ARE PRESENT

[75] Inventors: Guy Vanlerberghe, Claye-Souilly; Henri Sebag, Paris, both of France

[73] Assignee: L'Oreal, Paris, France

[21] Appl. No.: 56,110

[22] Filed: Jul. 9, 1979

[30] Foreign Application Priority Data

Jul. 13, 1978 [FR] France ................. 78 21082

[51] Int. Cl.³ .................. A61K 7/42; A61K 9/12; A61K 47/00
[52] U.S. Cl. .................. 424/47; 8/405; 8/406; 252/312; 424/59; 424/60; 424/61; 424/62; 424/63; 424/64; 424/70; 536/116; 514/943
[58] Field of Search ................. 424/47; 536/116

[56] References Cited

U.S. PATENT DOCUMENTS

| | | | |
|---|---|---|---|
| 1,959,930 | 5/1934 | Schmidt et al. | 424/358 |
| 1,970,578 | 8/1934 | Schoeller et al. | 424/358 |
| 2,612,509 | 9/1952 | Griffin | 424/358 X |
| 2,626,935 | 1/1953 | De Groote | 536/116 |
| 2,665,256 | 1/1954 | Barker | 424/358 X |
| 2,677,700 | 5/1954 | Jackson et al. | 424/358 X |
| 3,320,212 | 5/1967 | Shen et al. | 424/358 X |
| 4,199,562 | 4/1980 | Vanlerberghe et al. | 424/70 |

Primary Examiner—Dale R. Ore
Attorney, Agent, or Firm—Cushman, Darby & Cushman

[57] ABSTRACT

Surface-active statistical oligomers of the formula $$R_1O+[C_2H_3O(CH_2-X-R_2)O]_m[C_2H_3(CH_2-Y)O]_n+H \quad (I)$$

in which $R_1$ denotes a $C_4-C_{30}$ optionally substituted, aliphatic or cycloaliphatic radical, $R_2$ denotes a $C_5-C_{20}$ alkyl radical, m and n, which are identical or different, denote a number from 1 to 25, X denotes $-CH_2-$, $-O-$ or

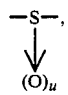

in which u=0 or 1, and Y denotes a group:

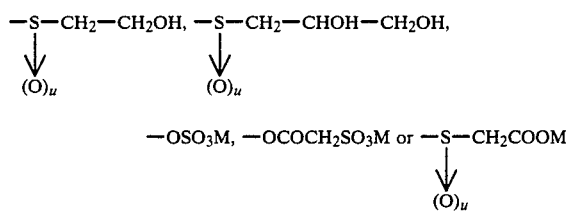

(in which M denotes a hydrogen atom or an alkali metal or alkaline earth metal), an amine group, an amine salt or ammonium are described as well as processes for their preparation and novel intermediates used in these processes. These surface-active oligomers possess a low aggressiveness towards the skin and mucous membranes and are suitable for use in cosmetic compositions and for dispersing hydrocarbons.

21 Claims, No Drawings

NEW SURFACE-ACTIVE STATISTICAL OLIGOMERS, A PROCESS FOR THEIR PREPARATION AND COMPOSITIONS IN WHICH THEY ARE PRESENT

DESCRIPTION

The present invention relates to surface-active oligomers obtained by statistical copolymerisation of (1) an epoxide compound, of lipophilic tendency, containing at least 8 carbon atoms, (2) an epoxide compound which generates water-soluble groups, and, optionally, (3) small proportions of a diepoxide compound which acts as a chain extender or crosslinking agent.

Most known surface-active agents consist of a lipophilic, aliphatic or arylaliphatic, fatty hydrocarbon chain joined to a hydrophilic block. These products have found numerous applications in a great variety of fields. They possess varied properties, depending on the nature of the hydrophilic block, but these properties are nevertheless restricted by the narrow choice available for the lipophilic part and by the conventional structure of their molecules, namely a juxtaposition of the hydrophilic part and the lipophilic part.

In order to broaden the field of application of surface-active agents, it has been proposed to replace the hydrocarbon chain of conventional surface-active agents by a lipophilic block obtained by the polymerisation of an alkylene oxide containing at least three carbon atoms. An account of this idea has been given in U.S. Pat. No. 2,677,700 and, according to a preferred embodiment, the lipophilic block is a polyoxypropylene chain. French patent application No. 2,359,165 also describes surface-active block oligomers possessing certain valuable properties.

We have now discovered, according to the present invention, that a statistical distribution of the units derived from two or three compounds with an epoxide group, rather than a distribution in the form of sequences or blocks, makes it possible further to improve certain physico-chemical properties for the same hydrophilic/lipophilic ratio. Thus, for example, the compounds of the present invention generally possess better solubility in water and better emulsifying or dispersing properties, especially towards hydrocarbons, than the corresponding surface-active block oligomers.

The present invention provides a surface-active statistical oligomer of the general formula (I):

$$R_1O+[C_2H_3(CH_2-X-R_2)O]_m[C_2H_3(CH_2-Y)O\!\!\dashv_{\!\overline{n}}\!\!]-H \quad (I)$$

$$\phantom{R_1O+[}(A)\phantom{xxxxxxxx}(B)$$

in which $R_1$ denotes an aliphatic or cycloaliphatic radical derived from substituted or unsubstituted, saturated or unsaturated, especially ethylenically unsaturated, acyclic or cyclic alcohol including, for example, a 1,2- or 1,3-diol, of formula $R_1OH$ having from 4 to 30 carbon atoms, preferably an alkyl or alkenyl radical having from 8 to 18 carbon atoms or a radical derived from a sterol, in particular from cholesterol or cholestanol or a hydrocarbon radical derived from alcohols of lanoline; $R_2$ denotes a linear or branched alkyl radical having from 5 to 20 carbon atoms, preferably from 7 to 16 carbon atoms; X denotes one of the following atoms or groups of atoms: $CH_2$, $O$ and

in which u denotes the number 0 or 1, m and n, which are identical or different, denote integers or decimal numbers from 1 to 25, the number n generally being equal to or greater than the number m which is preferably from 1 to 15; and Y denotes one of the groups:

—OH,  (a)

in which u denotes the number 0 or 1,

  (c)

in which u denotes the number 0 or 1 and $R_3$ and $R_4$, which are identical or different, denote alkyl or hydroxyalkyl radicals containing from 1 to 3 carbon atoms, preferably a methyl, ethyl or hydroxyethyl radical, or, alternatively, $R_3$ and $R_4$ form, together with the nitrogen atom to which they are attached, a heterocyclic ring having 5 or 6 ring members, preferably a piperidino or morpholino ring,

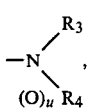  (d)

in which HV denotes an inorganic or organic acid, such as hydrochloric, hydrobromic, sulphuric, phosphoric, acetic, lactic, citric or tartaric acid, and $R_3$, u and $R_4$ have the meanings indicated for (c),

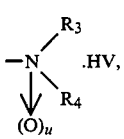  (e)

in which $R_5$ denotes a methyl, ethyl or hydroxyethyl radical, Z denotes an anion, such as $Cl^-$, $Br^-$, $I^-$, $CH_3SO_3^-$, $CH_3SO_4^-$ or $CH_3$—$C_6H_4$—$SO_3^-$, and $R_3$ and $R_4$ have the meanings indicated for (c),

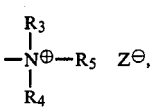  (f)

in which $Q^\ominus$ denotes an anion, such as $-CH_2COO^\ominus$, $-CH_2-CH_2COO^\ominus$ or $-(CH_2)_3SO_3^\ominus$, and $R_3$ and $R_4$ have the meanings indicated for (c), (g) —$OSO_3M$, in which M denotes a hydrogen atom or an alkali metal or alkaline earth metal, preferably sodium, potassium, calcium or magnesium, (h) —OCOCH₂SO₃M, in which M has the meaning indicated for (g), and

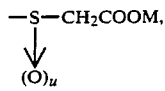

in which u denotes the number 0 or 1 and M has the meaning indicated for (h).

In an advantageous embodiment, $R_1$ denotes an alkyl radical having from 12 to 16 carbon atoms or a hydrocarbon radical derived from lanoline alcohols. In another advantageous embodiment, m denotes a number from 2 to 10 and n denotes a number from 3 to 20.

The unit —C₂H₃(CH₂XR₂)O— denotes the two isomers

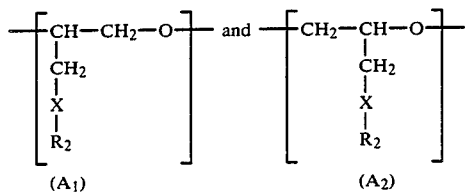

and the unit ─[C₂H₃(CH₂Y)O]─ denotes the two isomers

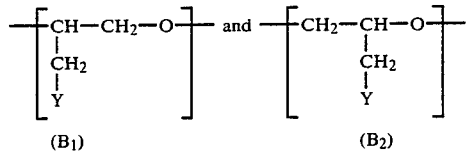

The two isomers $A_1$ and $A_2$, and also $B_1$ and $B_2$, correspond to the two ways in which the oxirane rings can be opened.

In the products according to the invention, the isomers $A_2$ and $B_2$ are predominant.

In the general formula (I), the large brackets which enclose the units A and B symbolise a statistical distribution of these two units and $R_1O$ represents a radical derived from a monoalcohol or from a 1,2- or 1,3-diol, which acts as an initiator in the polyaddition reactions leading to the compounds of the formula (I).

The invention also provides the products of the general formula (I) which have been modified by the action of a diepoxide which results in crosslinking and/or chain extension or branching.

The molar amount of crosslinking agent or chain extender, relative to the molar amounts of the units $(A_1)+(A_2)+(B_1)+(B_2)$, is less than or equal to 5 mols per 100.

Preferably the diepoxide is diepoxybutane, diglycidyl ether, the bis-glycidyl ether of bisphenol A i.e. bis glycidyl ether of 2,2 bis(4-hydroxyphenyl)propane and bis-epoxypropylpiperazine.

Amongst the products of the formula (I) and those modified by a diepoxide, there may advantageously be mentioned those in which Y denotes one of the groups:

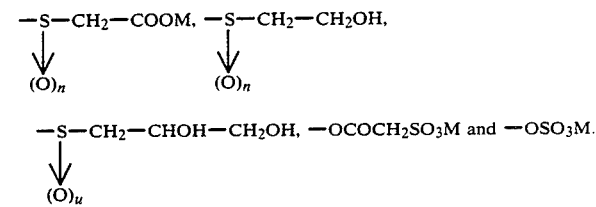

Another advantageous group is that in which Y denotes the group OH.

Another valuable group consists of the products in which Y denotes the group:

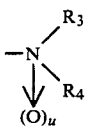

and more particularly:

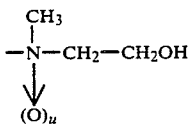

The products according to the invention can be obtained by the polyaddition, to a compound containing at least one hydroxyl group, which compound is referred to as an initiator, of a mixture of epoxides comprising: m molecules of an epoxide (1) containing 8 to 23 carbon atoms and optionally a hetero-atom such as oxygen or sulphur, n molecules of an epoxide (2) which generates hydrophilic groups, i.e. an epoxide possessing a group capable of being converted into a group of formula Y, and p molecules of a diepoxide compound (3) which acts as a chain extender or cross-linking agent, p being equal to 0 or to a maximum of 5% of (m+n).

The compounds acting as initiators in the polyaddition reactions are generally monoalcohols or 1,2- or 1,3-diols, which have from 4 to 30 carbon atoms and are aliphatic or are sterols such as cholesterol or cholestanol.

Type (1) epoxides include 1,2-alkylene oxides having 8 to 22, and advantageously from 10 to 22, carbon atoms, or alkyl glycidyl ethers or thioethers, in which the alkyl group contains from 5 to 20 carbon atoms and advantageously from 8 to 20 carbon atoms.

Type (2) epoxides include epihalogenohydrins, such as epichlorohydrin or epibromohydrin and tert.-butyl glycidyl ether, in which the halogen atom or the t-butoxy group can be replaced by water-solubilising groups.

Diepoxides (3) which may be mentioned include diepoxybutane, diglycidyl ether, the bis-glycidyl ether of bisphenol A and bis-epoxypropylpiperazine. It will be appreciated that cross-linking takes place with the hydroxyl groups which may be present in Y.

The polyaddition reactions can be carried out in the presence of an acid catalyst, such as $BF_3$, $SnCl_4$, $SbCl_5$ or $ZnCl_2$, or a basic catalyst, such as sodium hydroxide, methylate or ethylate or potassium hydroxide, methylate or ethylate, suitably in an amount from 0.05 to 5% by weight, relative to the reaction mixture.

Basic catalysts are preferably used with the alkyl glycidyl thioethers but are not used when the epoxide (2) is an epihalogenohydrin.

The polyaddition reactions are generally carried out at 40° to 160° C., and preferably at 40° to 110° C., in the presence of an acid catalyst, or at 110° to 160° C. in the presence of an alkaline catalyst.

The molar proportions of the epoxides (1)/(2)/(3) is suitably 1/1 to 8/0 to 0.45.

The mixtures of epoxides (1) and (2), or alternatively (1), (2) and (3), is conveniently introduced slowly, whilst stirring, so as to disperse them rapidly in the reaction medium. When a diepoxide (3) is used, the latter can also be introduced after the polyaddition reaction of the mixture of epoxides (1) and (2).

After the polyaddition reaction, the slightly condensed oligomers can be removed by molecular distillation.

The molecular weights of the intermediates is generally from 500 to 5,000.

If the epoxides (1) and (2) are used, the intermediates of the formula:

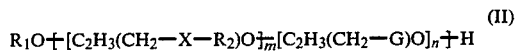
(II)

in which G denotes a halogen, in particular chlorine or bromine, or the tert.-butoxy radical, —O—C(CH$_3$)$_3$, and R$_1$, R$_2$, X, m and n have the meanings indicated for the formula (I), are obtained.

The unit $+C_2H_3(CH_2-X-R_2)O+$ denotes the two isomers A$_1$ and A$_2$ indicated above.

The unit $+C_2H_3(CH_2-G)O+$ denotes the two isomers

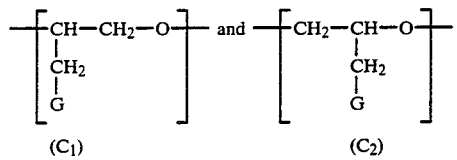

If the epoxides (1), (2) and (3) are used, crosslinked and/or branched or chain extended intermediates of the formula (II) are obtained.

Crosslinking consists in bridging two or several intermediate chains containing OH groups. Branching and chain extending are also initiated from OH group(s) present on the chain of the intermediate compounds.

This invention also provides the intermediates of the formula (II) and the intermediates of the formula (II) which have been crosslinked or branched by the introduction of a diepoxide, preferably of a diepoxide (3) indicated above.

To obtain the final product, the halogen atoms or the tert.-butoxy radicals represented by G in the intermediate of the formula (II) are replaced by one of the hydrophilic groups (a) to (i) indicated above.

The replacement of the halogen atoms by hydroxyl groups can be effected by reaction with an alkali metal salt of a carboxylic acid, preferably with sodium acetate or potassium acetate, at a temperature of, say, 150° to 200° C., in a suitable solvent, advantageously a glycol or glycol derivative; the acid ester formed is then saponified, for example with sodium hydroxide or potassium hydroxide, or subjected to alcoholysis by means of a lower (i.e. of 1 to 6 carbon atoms) alcohol, preferably methanol or ethanol, in the presence of a basic catalyst, preferably sodium methylate or ethylate or potassium methylate or ethylate. Such a process is described in greater detail in British Specification No. 1246929 or by U.S. Pat. No. 3,578,719, the disclosure of which is hereby incorporated by reference.

The replacement of the tert.-butoxy protective groups by hydroxyl groups can be effected by heating the intermediates at, say, 50° to 120° C. in the presence of a sulphocarboxylic acid, such as sulphoacetic acid, or of a sulphonic acid, such as benzenesulphonic acid or p-toluene-sulphonic acid. This process is described in greater detail in British Specification No. 1267259 and U.S. Pat. Nos. 3,840,606 and 3,959,390, the disclosure of which is hereby incorporated by reference.

The replacement of the halogen atoms in the halogeno-propoxy unit by thiohydroxyethyl groups

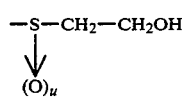

or thiodihydroxypropyl groups

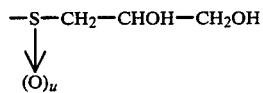

can be effected by heating the intermediate of the formula (II), in which G denotes a halogen, with 2-mercaptoethanol or 3-mercaptoglycerol, at a temperature of, say, 20°-150° C., in the presence of an alkaline compound which is advantageously sodium hydroxide, methylate or ethylate or potassium hydroxide, methylate or ethylate, this optionally being followed by oxidation which is preferably carried out by means of hydrogen peroxide, at a temperature of 0° to 50° C, preferably 30° to 40° C., preferably in stoichiometric proportions and advantageously in the presence of acetic acid. Such a process is described in greater detail in British Specification No. 1,229,525 and U.S. Pat. No. 3,906,048, the disclosure of which is hereby incorporated by reference.

These compounds containing thiohydroxyethyl or thiodihydroxypropyl groups can also be obtained by reacting a mercaptan of the formula HS—CH$_2$—CH$_2$OH or HS—CH$_2$—CHOH—CH$_2$OH, in the presence of sodium methylate or ethylate or potassium methylate or ethylate, with the intermediate of the formula

(III)

in which R$_6$ denotes CH$_3$—SO$_2$— or CH$_3$—C$_6$H$_4$—SO$_2$—, these intermediates being obtained by reacting mesyl chloride, CH$_3$—SO$_2$Cl, or tosyl chloride, CH$_3$—C$_6$H$_4$—SO$_2$Cl, with the product of the formula (I) in which Y denotes OH.

The products of the formula (I) in which Y denotes the group

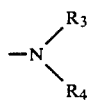

can be obtained by heating the intermediates of the formula (II) in which G denotes chlorine or bromine, or the intermediates of the formula (III), with a secondary amine

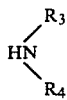

in which $R_3$ and $R_4$ have the meanings indicated above, optionally in the presence of a solvent, preferably a glycol or alkoxyethanol, at atmospheric pressure or in an autoclave, at a temperature of, say, 50° to 160° C. Oxidation with hydrogen peroxide or a per-acid, such as peracetic or performic acid, at a temperature of 10° to 100° C., yields the corresponding amine oxides, that is to say the products of the formula (I) in which Y denotes

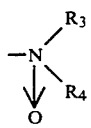

The products of the formula (I) in which Y denotes the group

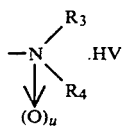

can be obtained by salifying the above compounds with an inorganic or organic acid, preferably with hydrochloric, hydrobromic, sulphuric, phosphoric, acetic, lactic, citric or tartaric acid, optionally in the presence of a solvent, especially an alcohol preferably having from 1 to 4 carbon atoms, thus ensuring the homogeneity of the reaction medium.

The products of the formula (I) in which Y denotes the group

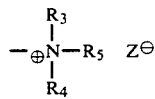            (e)

can be obtained by alkylating the products of the formula (I) in which Y denotes a group

with methyl chloride, bromide, iodide, sulphate, mesylate or tosylate or with glycol chlorohydrin. When $Z^-$ denotes a mesylate or tosylate anion, these products can also be obtained by reacting the intermediate of the formula (III) with a tertiary amine of the formula:

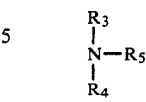

in which $R_3$, $R_4$ and $R_5$ have the meanings indicated above.

The products of the formula (I) in which Y denotes the group

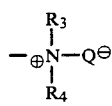

can be obtained by alkylating the products of the formula (I) in which Y denotes the group

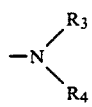

with methyl chloroacetate or chloropropionate or ethyl chloroacetate or chloropropionate or with the corresponding sodium or potassium salts, or with propanesultone (when $Q^-$ denotes the propylsulphonate anion).

The products of the formula (I) in which Y denotes the group

            (g)

can be obtained by sulphating a product of the formula (I), in which Y denotes OH, with chlorosulphonic acid, optionally in the presence of a solvent which is preferably chloroform, dichloroethane, benzene or toluene. If M denotes an alkali metal or alkaline earth metal, the resulting acid can be neutralised by the appropriate base.

The products of the formula (I) in which Y denotes the group

            (h)

can be obtained by esterifying a product of the formula (I), in which Y denotes OH, with sulphoacetic acid, the acid formed optionally being neutralised with an alkali metal base or alkaline earth metal base. It is also possible to obtain these products by reacting sulphoacetic acid in stoichiometric amounts directly with the intermediate of the formula (II) in which G denotes a tert.-butoxy radical.

The products of the formula (I) in which Y denotes the group:

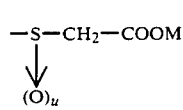            (i)

can be obtained by reacting the intermediates of the formula (II), in which G denotes a halogen, with methyl or ethyl thioglycolate, in the presence of sodium methylate, which acts as a catalyst, and of an alcohol having from 1 to 4 carbon atoms, which acts as a solvent, at a temperature of 80° to 120° C., this being followed, in the case where u denotes 1, by oxidation with hydrogen peroxide or a per-acid.

The products of the formula (I) in which Y denotes the group (i) can also be prepared by reacting ethyl or methyl thioglycolate with products of the formula (III), in the presence of sodium methylate or ethylate or potassium methylate or ethylate, in solvents such as ethers, chloro-hydrocarbons or aromatic hydrocarbons.

The resulting ester can be saponified and acidified to give the corresponding acid. The alkali metal salt or alkaline earth metal salt can be obtained by neutralising the acid with the corresponding base. If the epoxide (1) is an alkyl glycidyl thioether, that is to say if X denotes —S— in the formula (I), and if Y denotes a thioether group and the latter is oxidised to a sulphoxide group, the atom —S— is also converted to a sulphoxide group

The products of the formula (I) in which Y denotes the group OH or

at least one of the groups $R_3$ or $R_4$ denoting hydroxyalkyl, can be rendered more water-soluble by the polyaddition of 1-20 mols of ethylene oxide or glycidol, the hydroxyl groups acting as initiators. By this means the said OH groups are converted into groups of formula $-O(C_2H_4O)_rH$ and $-O[C_2H_3(CH_2OH)O]_rH$, respectively where r is 1-20.

The products of the formula (I) are generally in the form of viscous oils or of water-soluble or water-dispersible pastes. They generally have a molecular weight of 500 to 5,000. They can be used in various industries as surface-active agents and especially as low-foaming agents, wetting agents, detergents, emulsifiers, peptising agents, dispersing agents, binders, anti-caking agents, solubilising agents, penetrating agents, agents for preventing redeposition, flotation agents, as antistatic finishes, and as dyeing auxiliaries.

The present invention also provides a composition, which can be used in various industries, containing at least $0.5.10^{-3}\%$ by weight of a product of the formula (I). The proportion of product of the formula (I) in the compositions can range up to, say, 80% by weight.

The products of the formula (I) possess low aggressiveness towards the skin and the mucous membranes. Their molecular weight and their low aggressiveness are such that the products of the formula (I) are of particular value as additives for cosmetic compositions or as excipients for pharmaceutical compositions.

The present invention also provides pharmaceutical compositions which contain, as excipient, at least one product of the formula (I).

The present invention also provides cosmetic compositions which contain at least one product of the formula (I). The cosmetic compositions are, in particular, compositions intended for the care of the skin, nails and hair.

Such hair-care compositions include, in particular, washing compositions, especially shampoos, and hair-conditioning compositions and dyeing compositions.

The shampoos can contain, in addition to the surface-active statistical oligomer, one or more anionic, cationic, amphoteric or non-ionic surface-active agents and also other cosmetic adjuvants.

The cosmetic compositions are suitably presented in the form of an aqueous or aqueous-alcoholic solution or in the form of a cream, a gel, an emulsion or an aerosol.

The cosmetic and pharmaceutical compositions generally contain the products of the formula (I) in an amount from 0.0005 to 80% and advantageously 0.5 to 40%, by weight relative to the total weight of the composition.

The products of the formula (I) can be used in these compositions as surface-active agents, either by themselves or mixed with anionic, cationic, non-ionic or amphoteric surface-active compounds.

The compositions can additionally contain acids or bases, foam synergistic agents, foam stabilisers, thickeners, opacifiers, sequestering agents, superfatting agents, antiseptics, preservatives, treating products, polymers, pigments, perfumes, dyestuffs, solvents for dyestuffs, sun filters, oxidising agents and other adjuvants which are usually employed in cosmetic compositions, especially hair compositions.

The acids and bases are used in an amount suitable for adjusting the pH of the compositions to, say, 3 to 12 and preferably 3 to 10.

The present invention also relates to the use of the oligomers of the formula (I) for the dispersion of hydrocarbons. From 1 to 50%, preferably from 5 to 20%, of oligomer, relative to the weight of the hydrocarbon to be dispersed, is generally used.

The dispersing or emulsifying power and the stability of the resulting dispersion or emulsion varies depending on the nature of the hydrocarbon and the value of $R_1$, $R_2$, X, Y, m and n in the oligomer.

The ability of the oligomers of the formula (I) to disperse or emulsify hydrocarbons can be utilised in various applications, such as the cleaning of containers, for example vats or tanks, containing hydrocarbons. For such applications, it is sufficient if the dispersion formed is stable for the time required for cleaning. However, the stability of the dispersion must be sufficient to permit this cleaning.

The oligomer or mixture of oligomers which is most suitable for the hydrocarbon to be dispersed is chosen on the basis of a simple test such as that described in Example 31 below.

The invention is further illustrated in the following Examples.

EXAMPLE 1

Preparation of a mixture of cationic oligomers of the general formula I in which $R_1$ denotes the radical $C_{12}H_{25}$, $R_2$ denotes the radical $C_{12}H_{25}$, X denotes an oxygen atom, Y denotes the group

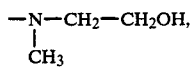

$m=5$ and $n=15$.

(a) Preparation of the corresponding polychloropropyleneoxy intermediate derivatives 2.1 ml of $BF_3$ etherate are added at 60° C., whilst stirring, to 28 g (0.15 mol) of dodecanol sold under the tradename "Alfol 12", and a mixture containing 188 g (0.75 mol) of dodecyl glycidyl ether and 207 g (2.25 mols) of epichlorohydrin are added in the space of 4 hours. Stirring is continued for 2 hours at 60° C.

After the epoxide groups have disappeared, the reaction mixture is washed with three times 400 ml of boiling water. After drying by heating under reduced pressure, the mixture is topped, that is to say the most volatile constituents are removed by molecular distillation, at a temperature of 227° C. under a pressure of $10^{-3}$ mm Hg.

The product thus obtained is in the form of an amber oil having a molecular weight of 2,000, as measured by the vapour pressure lowering method.

Organic Cl: 5.3 meq/g (milliequivalents/gram).

(b) Preparation of the cationic oligomers 53 g (0.67 mol) of methylethanolamine are added to 50 g (270 meq of chlorine) of the derivative thus obtained, and the mixture is heated for 6 hours at 130° C. under a nitrogen atmosphere.

The reaction mixture is washed with three times 100 ml of water at 85° C. The first washing is carried out in the presence of 30 ml of n-butanol in order to improve decantation.

After drying under reduced pressure, a thick, orange-yellow, water-soluble oil is obtained.

Base number: 4.02 meq/g.

EXAMPLE 2

Preparation of a mixture of non-ionic oligomers of the general formula I in which $R_1$ and $R_2$ denote the radical $C_{12}H_{25}$, X denotes an oxygen atom, Y denotes the group OH, m=5 and n=15.

50 g of dipropylene glycol and 27.8 g of potassium acetate are added to 50 g (270 meq of Cl) of the polychloropropyleneoxy derivative prepared in Example 1a, and the mixture is heated for 7 hours at 180° C., whilst stirring.

The potassium chloride formed is then filtered off and the dipropylene glycol is subsequently removed by heating under reduced pressure.

60 ml of absolute ethanol and 0.39 g of a solution of sodium methylate containing 5.72 meq/g (in methanol) are added to the product thus obtained.

The solution is left to stand for 12 hours at ambient temperature and the ethanol is then removed by heating under reduced pressure.

The resulting product is in the form of a water-dispersible oil which is deep brown in colour.

EXAMPLE 3

Preparation of a mixture of cationic oligomers of the general formula I in which $R_1$ and $R_2$ denote the radical $C_{12}H_{25}$, X denotes an oxygen atom, Y denotes the group

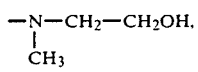

m=5 and n=15, which oligomers are cross-linked with the bis-glycidyl ether of bisphenol A, p being equal to 0.6.

6.4 g (5.61 meq/g) of the bis-glycidyl ether of bisphenol A (sold under the trademark "Epikote 827"), dissolved in about 7 g of chloroform, are added to 84 g of the crude polychloropropyleneoxy derivative (not washed and not topped by molecular distillation) prepared as in Example 1(a) and having a molecular weight of 935.

The addition is carried out at a temperature of 50°–55° C. in the course of about 20 minutes. After stirring for 30 minutes, thickening of the reaction medium is observed.

After washings with hot water and topping by molecular distillation, a product having a molecular weight of 1,515 is obtained.

40 g (about 0.5 mol) of methylethanolamine are added to 40 g (about 200 meq of chlorine) of the derivative thus obtained, and the mixture is then heated for 6 hours at 130° C. under a nitrogen atmosphere.

Determination of the ionised chlorine: 2.47 meq/g.

The mixture is washed three times with 100 ml of hot water and then dried by heating under reduced pressure.

A very thick, amber-coloured, water-soluble oil is thus obtained.

Base number: 3.93 meq/g.

EXAMPLE 4

Preparation of a mixture of non-ionic oligomers of the general formula I in which $R_1$ denotes the radical $C_{12}H_{25}$, $R_2$ denotes the radical $C_8H_{17}$, X denotes the group —$CH_2$—, Y denotes the group —OH, m=4 and n=15.

(a) Preparation of the corresponding polyoxypropyleneoxy intermediate derivatives 1.39 ml of $BF_3$ etherate are added, at 55° C., to 18.6 g (0.1 mol) of dodecanol (sold under the trademark "Alfol 12"), and a mixture containing 73.6 g (0.4 mol) of 1,2-epoxydodecane and 139 g (1.5 mols) of epichlorohydrin is then added in the space of 3 hours.

The mixture is then stirred for 2 hours at 55°–60° C.

After the epoxide groups have disappeared, the reaction mixture is washed with three times 300 ml of boiling water. After drying by heating under reduced pressure, the most volatile constituents are removed by molecular distillation at a temperature of 225° C. under a pressure of $10^{-3}$ mm Hg.

The product thus obtained is in the form of a yellow-coloured oil having a molecular weight of 1,050, as measured by the vapour pressure lowering method.

Determination of the organic chlorine: 6.6 meq/g.

(b) Preparation of the non-ionic oligomers 68.5 g (about 700 meq) of potassium acetate are added to 100 g (660 meq of chlorine) of the derivative thus obtained, dissolved in 100 g of dipropylene glycol, and the mixture is then heated under a nitrogen atmosphere for 7 hours at 180° C.

The amount of ionised chlorine is then 2.48 meq/g and the base number is 0.2 meq/g.

After filtering off the inorganic salts, the solvent is removed by heating under reduced pressure.

The reaction mixture is taken up in 110 ml of absolute ethanol. 1.1 g of sodium methylate in methanol (5.5 meq) are added and the mixture is left to stand overnight at ambient temperature.

After filtration, the solvents are removed by evaporation under reduced pressure.

The resulting product is in the form of a soft brown paste which is readily dispersible in water. Hydroxyl number: 7.8 meq/g.

EXAMPLE 5

Preparation of a mixture of cationic oligomers of the general formula I in which $R_1$ denotes the radical $C_{12}H_{25}$, $R_2$ denotes the radical $C_8H_{17}$, X denotes the group —$CH_2$—, Y denotes the group

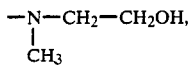

$m=5$ and $n=15$.

(a) Preparation of the corresponding polychloropropyleneoxy intermediate derivatives 1.13 ml of $BF_3$ etherate are added, at 60° C., to 13.9 g (0.075 mol) of dodecanol (Alfol 12), and a mixture containing 69 g (0.375 mol) of 1,2-epoxydodecane and 104 g (1.125 mols) of epichlorohydrin is added in the space of 4 hours. The mixture is stirred for 2 hours at 60° C.

After the epoxide groups have disappeared, the reaction mixture is washed with three times 200 ml of boiling water. After drying by heating under reduced pressure, the most volatile compounds are removed by molecular distillation at a temperature of 250° C. under a pressure of $10^{-3}$ mm Hg.

The product thus obtained is in the form of an amber oil having a molecular weight of 1,225, as measured by the vapour pressure lowering method.

Organic chlorine: 6.15 meq/g.

(b) Preparation of the cationic oligomers 62 g (0.77 mol) of methylethanolamine are added to 50 g (307 meq of organic chlorine) of the polychlorinated derivatives prepared above, and the mixture is heated under a nitrogen atmosphere for 5½ hours at 130° C.

Ionised chlorine number: 2.7 meq/g.

The reaction mixture is subsequently washed three times with 150 ml of boiling water and then dried under reduced pressure.

A thick, amber-coloured oil is thus obtained which dissolves in water to form a solution possessing a very slight turbidity which disappears on adding a small amount of an acid such as hydrochloric acid or lactic acid.

Base number: 4.5 meq/g.

EXAMPLE 6

Preparation of a mixture of non-ionic oligomers of the general formula I in which $R_1$ denotes the radical $C_{12}H_{25}$, $R_2$ denotes the radical $C_8H_{17}$, X denotes the group —$CH_2$—, Y denotes the group OH, $m=5$ and $n=15$.

20 g of dipropylene glycol and 12.65 g of potassium acetate are added to 20 g (125 meq of chlorine) of the polychloropropyleneoxy derivative (prepared in Example 5a), and the mixture is heated, whilst stirring and under a nitrogen atmosphere, for 7 hours at 180° C.

The inorganic salts are subsequently removed by filtration and the solvent is then removed by heating under reduced pressure.

25 ml of absolute ethanol and 0.16 g of a solution of sodium methylate (5.7 meq/g) in methanol are added to the product thus obtained, and the solution is left for about 12 hours at ambient temperature.

The solvent is then removed by heating under reduced pressure.

The resulting product is in the form of a very thick, deep-coloured oil which dissolves in water to give a slight opalescence.

Hydroxyl number: 7.94 meq/g.

EXAMPLE 7

Preparation of a mixture of cationic oligomers of the general formula I in which $R_1$ denotes the radical $C_{12}H_{25}$, $R_2$ denotes the radical $C_8H_{17}$, X denotes the group —$CH_2$—, Y denotes the group

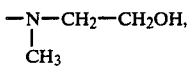

$m=5$ and $n=15$, which oligomers are crosslinked with the bis-glycidyl ether of bisphenol A, p being equal to 0.6.

(a) Preparation of the polychlorinated intermediate derivatives 1.1 ml of boron trifluoride etherate are added to 14 g (0.075 mol) of dodecanol (Alfol 12), and a mixture containing 69 g (0.375 mol) of 1,2-epoxydodecane, 104 g (1.125 mols) of epichlorohydrin and 16 g (0.045 mol) of the bis-glycidyl ether of bisphenol A (sold under the trademark "Epikote 827") is then added dropwise at a temperature of 60° C.

The catalyst is preferably introduced in two or three portions during the addition of the epoxide mixture.

Duration of the addition: 4 hours.

After the epoxide groups have disappeared, the reaction mixture is washed three times with 200 ml of boiling water.

After drying under reduced pressure, the volatile compounds are removed by molecular distillation at 225° C. under a pressure of $10^{-3}$ mm Hg; about 16% of the total mixture is thus distilled.

The resulting residue then has a molecular weight of 2,300.

Organic chlorine: 5.5 meq/g.

(b) Preparation of the cationic oligomers 67 g (0.83 mol) of methylethanolamine are added to 60 g (330 meq of chlorine) of the intermediate thus prepared, and the mixture is then heated for 4½ hours at 130° C.

The reaction mixture is washed three times with 150 ml of water at 90° C. in the presence of n-butanol.

After drying by heating under reduced pressure, a thick, water-soluble oil is obtained.

Base number: 4.2 meq/g.

EXAMPLE 8

Preparation of a mixture of non-ionic oligomers of the general formula I in which $R_1$ denotes the radical $C_{12}H_{25}$, $R_2$ denotes the radical $C_8H_{17}$, X denotes the group —$CH_2$—, Y denotes the group OH, $m=5$ and n=15, which oligomers are crosslinked with the bis-glycidyl ether of bisphenol A, p being equal to 0.6.

50 g of dipropylene glycol and 28.5 g (290 meq) of potassium acetate are added to 50 g (275 meq of chlorine) of the polychlorinated derivative prepared in Example 7a, and the mixture is then heated under a nitrogen atmosphere for 7 hours at 180° C.

Ionised chlorine number: 2.18 meq/g.

The inorganic salts are removed by filtration and the solvent is then evaporated off under reduced pressure.

The residue is taken up in 65 ml of absolute alcohol and, after adding 0.4 g (2.25 meq) of sodium methylate in methanol, the mixture is left to stand for about fifteen hours at ambient temperature.

The mixture is filtered and the solvent is then distilled under reduced pressure.

A thick, brown, water-dispersible oil is thus obtained.
Hydroxyl number: 6.6 meq/g.

EXAMPLE 9

Preparation of a mixture of cationic oligomers of the general formula I in which $R_1$ denotes the group $C_{12}H_{25}$, $R_2$ denotes the group $C_8H_{17}$, X denotes the group —$CH_2$—, Y denotes the group

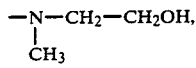

m=5 and n=15, which oligomers are crosslinked with the bis-glycidyl ether of bisphenol A, p being equal to 1.

(a) Preparation of the intermediates 1.2 ml of $BF_3$ etherate and a mixture containing 69 g (0.375 mol) of 1,2-epoxydodecane, 104 g (1.125 mols) of epichlorohydrin and 26.7 g (0.075 mol) of the bis-glycidyl ether of bisphenol A (sold under the trademark "Epikote 827") are added at 60° C., in two stages, to 14 g (0.075 mol) of dodecan-1-ol. (The second portion of catalyst is introduced after the addition of the first half of the epoxide mixture).

The product thus obtained is in the form of a gel having a molecular weight of 2,350.

(b) Preparation of the cationic oligomers 53 g (0.66 mol) of methylethanolamine are added to 50 g (263 meq of chlorine) of the polyhalogenated derivative thus obtained.

After 6 hours at 130° C., the degree of substitution is virtually quantitative.

After washing and drying, a soft, amber-coloured paste is obtained which dissolves in water to give a very slight turbidity which disappears on adding a small amount of acid.

Base number: 3.95 meq/g.

EXAMPLE 10

Preparation of a mixture of non-ionic oligomers of the formula (I) in which $R_1$ denotes the group $C_{12}H_{25}$, $R_2$ denotes the group $C_8H_{17}$, X denotes the group —$CH_2$—, Y denotes the group —OH, m=5 and n=15, which oligomers are cross-linked with the bis-glycidyl ether of bisphenol A, p being equal to 1.

50 g of dipropylene glycol and 30 g of potassium acetate are added to 50 g (263 meq of chlorine) of the polyhalogenated derivatives prepared in accordance with Example 9(a).

After heating for 6 hours at 180° C., removal of the inorganic salts by filtration, distillation of the solvent and alcoholysis with ethanol in the presence of 0.4 g of sodium methylate, an elastic mixture is isolated.

Hydroxyl number: 6.2 meq/g.

EXAMPLE 11

Preparation of a mixture of cationic oligomers of the general formula I in which $R_1$ denotes the radical $C_{12}H_{25}$, $R_2$ denotes the radical $C_8H_{17}$, X denotes the group $CH_2$, Y denotes the group

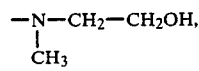

m=10 and n=15.

(a) Preparation of the corresponding polychloropropyleneoxy intermediate derivatives 1.5 ml of $BF_3$ etherate are added, at 60° C., to 9.3 g (0.05 mol) of dodecan-1-ol (sold under the trademark "Alfol 12"), and a mixture containing 92 g (0.5 mol) of 1,2-epoxydodecane and 69.4 g (0.75 mol) of epichlorohydrin is added in the space of 4 hours.

The mixture is then stirred for 2 hours at 60° C.

After the epoxide groups have disappeared, the reaction mixture is washed with three times 200 ml of boiling water, and then, after drying by heating under reduced pressure, the most volatile compounds are removed by molecular distillation at a temperature of 227° C. under a pressure of $10^{-3}$ mm Hg.

The product thus obtained has the appearance of an amber oil, the molecular weight of which is 1,600, as measured by the vapour pressure lowering method.

Organic chlorine: 4.4 meq/g.

(b) Preparation of the cationic oligomers 35.5 g (0.43 mol) of methylethanolamine are added to 40 g (175 meq of chlorine) of the intermediate derivatives thus prepared, and the mixture is heated at 130° C. for 8 hours.

The extent of reaction is then 98%.

Ionised chlorine number: 2.27 meq/g.

After washing in the presence of n-butanol at 90° C. and drying under reduced pressure, an amber oil is obtained which dissolves in water to give a slight turbidity. This turbidity disappears on adding a small amount of acid.

Base number: 3.35 meq/g.

EXAMPLE 12

Preparation of a mixture of non-ionic oligomers of the general formula I in which $R_1$ denotes the radical $C_{12}H_{25}$, $R_2$ denotes the radical $C_8H_{17}$, X denotes the group —$CH_2$—, Y denotes the group —OH, m=10 and n=5.

50 g of dipropylene glycol and 22.7 g of potassium acetate are added to 50 g (220.5 meq of chlorine) of the polychloropropyleneoxy derivatives prepared in Example 11(a), and the mixture is stirred under a nitrogen atmosphere for 7 hours at 180° C.

The inorganic salts are then removed by filtration and the solvent is removed by distillation under reduced pressure.

60 ml of absolute ethanol and 0.4 g of a solution of sodium methylate containing 5.7 meq/g are added to the product thus obtained, and the solution is then left for about 12 hours at ambient temperature. The solvent is then removed by heating under reduced pressure.

The final product is in the form of a very thick, amber-coloured, water-dispersible oil.

Hydroxyl number: 6 meq/g.

EXAMPLE 13

Preparation of a mixture of non-ionic oligomers of the general formula I in which $R_1$ denotes a mixture of radicals $C_{12}H_{25}$ and $C_{14}H_{29}$, in the proportion of about 55/45, $R_2$ denotes a mixture of radicals $C_7H_{15}$ to $C_{10}H_{21}$, X denotes the group —$CH_2$—, Y denotes the group —OH, m=5 and n=15.

(a) Preparation of the corresponding polychloropropyleneoxy intermediates 1.75 ml of $BF_3$ are added, in several portions, to 19.5 g (0.1 mol) of a mixture of dodecan-1-ol and tetradedan-1-ol, and a mixture containing 107 g (0.5 mol) of a $C_{11}$ to $C_{14}$ 1,2-epoxyalkane, sold under the trademark "Nedox 114", and 139 g (1.5 mols) of epichlorohydrin is added dropwise, at 70° C., in the space of 3 hours.

After washings and distillation of the volatile compounds at 215° C. under a pressure of $10^{-3}$ mm Hg, a product is obtained which is deep brown in colour and has a molecular weight of 1,320.

Organic chlorine: 5.6 meq/g.

(b) Preparation of the non-ionic oligomers 80 g of dipropylene glycol and 48 g of potassium acetate are added to 80 g (463 meq of chlorine) of the product thus obtained.

After heating for 6 hours at 180° C., the ionised chlorine number is 2.2 meq/g.

After removing the inorganic salts by filtration and evaporating off the solvent, the residue is taken up in 100 ml of absolute ethanol in the presence of 0.7 g (3.6 meq) of sodium methylate dissolved in methanol.

The mixture is left overnight at ambient temperature and the solvent is then driven off under reduced pressure.

A deep brown oil is thus obtained which dissolves in water to give a slight opalescence.

EXAMPLE 14

Preparation of a mixture of cationic oligomers of the general formula I in which $R_1$ denotes the radical $C_{16}H_{33}$, $R_2$ denotes the radical $C_{12}H_{25}$, X denotes the group —$CH_2$—, Y denotes the group

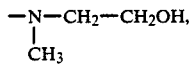

m=4 and n=20, which oligomers are crosslinked with the bis-glycidyl ether of bisphenol A, p being equal to 0.7.

(a) Preparation of a mixture of polychlorinated intermediates 1.8 ml of $BF_3$ etherate are added at 60°–70° C., in several portions, to 24 g (0.1 mol) of hexadecanol sold under the trademark "Alfol 16 RD", and a mixture containing 107 g (0.4 mol) of 1,2-epoxyhexadecane, 185 g (2 mols) of epichlorohydrin and 25.5 g (0.07 mol) of the bis-glycidyl ether of bisphenol A (sold under the trademark "Epikote 827") is added dropwise in the space of 3 hours.

The temperature and stirring are maintained for a further 4 hours.

After the epoxide groups have disappeared, the product is washed and dried and the volatile compounds, representing about 15% of the reaction mixture, are then removed at 225° C. under a pressure of $10^{-3}$ mm Hg.

Molecular weight: 2,160.

Organic chlorine: 6 meq/g.

(b) Preparation of the cationic oligomers 84 g (1.05 mols) of methylethanolamine are added to 70 g (420 meq of chlorine) of the intermediate derivatives thus obtained, and the mixture is then heated at 130° C. under a nitrogen atmosphere for 5 hours.

Ionised chlorine number: 2.7 meq/g.

After washing with boiling water in the presence of n-butanol, a very thick, water-soluble oil is obtained which is orange-yellow in colour.

Base number: 4.3 meq/g.

EXAMPLE 15

Preparation of a mixture of non-ionic oligomers of the general formula I in which $R_1$ denotes the radical $C_{16}H_{33}$, $R_2$ denotes the radical $C_{12}H_{25}$, X denotes the group —$CH_2$—, Y denotes the group —OH, m=4 and n=20, which oligomers are crosslinked with the bis-glycidyl ether of bisphenol A, p being equal to 0.7.

50 g of dipropylene glycol and 31 g (315 meq) of potassium acetate are added to 50 g (300 meq of chlorine) of the polychlorinated intermediates prepared in Example 14(a), and the mixture is heated at 185° C. under a nitrogen atmosphere for 7 hours.

After removing the inorganic salts and the solvents, and after alcoholysis with ethanol, as in the above examples, a pasty product is obtained which is deep brown in colour and dissolves in water to give a slight turbidity.

The cloud point is 43° C., as measured in water at a concentration of 0.5%.

Hydroxyl number =7.5 meq/g.

EXAMPLE 16

Preparation of a mixture of anionic oligomers of the general formula I in which $R_1$ denotes the radical $C_{16}H_{33}$, $R_2$ denotes the radical $C_{12}H_{25}$, X denotes the group $CH_2$, Y denotes the group —S—$CH_2$—COOH, m=4 and n=20, which oligomers are crosslinked with the bis-glycidyl ether of bisphenol A, p being equal to 0.7.

40 g of dipropylene glycol, 44 g of ethyl thioglycolate and 80 g (384 meq) of sodium methylate in methanol are added to 55 g (330 meq of organic chlorine) of the polychlorinated intermediates prepared in accordance with Example 14(a).

The reaction mixture is heated under reflux for 5 hours and is then taken up in 345 ml of normal hydrochloric acid to which 150 ml of water have been added.

The polyacids thus prepared are salted out and washed in the presence of chloroform.

After drying, the resulting product is in the form of a very thick oil which is soluble in slightly warm water.

Acid number: 4 meq/g.

EXAMPLE 17

Preparation of a mixture of non-ionic oligomers of the formula I in which $R_1$ and $R_2$ denote the 2-ethylhexyl radical, X denotes an oxygen atom, Y denotes the group —OH, m=6 and n=20.

(a) Preparation of a mixture of intermediates 1 ml of $BF_3$ etherate is added to 6.5 g (0.05 mol) of 2-ethylhexanol, and a mixture containing 130 g (1 mol) of tert.-butyl glycidyl ether and 59 g (0.3 mol) of 2-ethylhexyl glycidyl ether is then added, at 65° C., in the course of 3 hours.

After washings, drying and removal of the volatile products by molecular distillation at 210° C. under a pressure of $10^{-3}$ mm Hg, an intermediate having a molecular weight of 1,600 is obtained.

(b) Preparation of the non-ionic oligomers

By heating 80 g of the intermediate derivatives thus obtained, for 3 hours at 90°–100° C. in the presence of 0.8 g of sulphoacetic acid, a very thick, black-coloured oil is obtained which dissolves in water to give a very slight turbidity.

Hydroxyl number 7.5 meq/g.

EXAMPLE 18

Preparation of a mixture of non-ionic oligomers of the general formula I in which $R_1$ and $R_2$ denote the 2-ethylhexyl radical, X denotes an oxygen atom, Y denotes the group —OH, m=2 and n=8.

(a) Preparation of a mixture of intermediates 0.75 ml of $BF_3$ etherate is added to 13 g (0.1 mol) of 2-ethylhexanol, and a mixture containing 104 g (0.8 mol) of tert.-butyl glycidyl ether and 39 g (0.2 mol) of 2-ethylhexyl glycidyl ether is then added at 65°–70° C.

The reaction is carried out as in Example 17.

A mixture of intermediates having a molecular weight of 1,075 is thus obtained.

(b) Preparation of the non-ionic oligomers 50 g of this mixture are heated at 100° C. for 2 to 3 hours in the presence of 0.5 g of sulphoacetic acid and 2 ml of water.

The resulting product is in the form of a black-brown paste which dissolves in water to give a slight opalescence.

Hydroxyl number 7.6 meq/g.

EXAMPLE 19

Preparation of a mixture of anionic oligomers of the formula I in which $R_1$ denotes the radical $C_{12}H_{25}$, $R_2$ denotes the radical $C_{12}H_{25}$, X denotes a sulphur atom, Y denotes the group —OCO—$CH_2$—$SO_3H$, m=3 and n=3.

1 g of a solution of sodium methylate containing 5.4 meq/g is added to 4.65 g (0.025 mol) of dodecan-1-ol (sold under the trademark "Alfol 12"), and a mixture of 20 g (0.075 mol) of dodecyl glycidyl thioether and 9.75 g (0.075 mol) of tert.-butyl glycidyl ether is then added, at a temperature of 150° C. and in the space of 1 hour 15 minutes, under a nitrogen atmosphere.

The temperature is then kept at 150° C. for 4 hours.

11.7 g (0.075 mol) of sulphoacetic acid are added to 25 g (75 meq of hydroxyl groups) of the intermediates thus obtained, and the reaction medium is heated at 115°–120° C. for 1 hour 30 minutes at atmospheric pressure and then for 30 minutes under reduced pressure.

A brown, water-dispersible paste is thus obtained.

Acid number: 2.1 meq/g.

EXAMPLE 20

Preparation of a mixture of non-ionic compounds of the general formula I in which $R_1$ and $R_2$ denote the radical $C_{12}H_{25}$, X denotes a sulphur atom, Y denotes the group —OH, m=2 and n=12.

2 g of a solution of sodium methylate containing 5.4 meq/g are added, in portions, to 4.65 g (0.025 mol) of dodecan-1-ol (sold under the trademark "Alfol 12"), and a mixture containing 13.4 g (0.05 mol) of dodecyl glycidyl thioether and 39 g (0.3 mol) of tert.-butyl glycidyl ether is added dropwise, at 150° C., in the space of 1 hour 30 minutes.

The resulting product is washed twice with 60 ml of boiling water and then dried by heating under reduced pressure. The volatile compounds are then removed by molecular distillation.

0.36 g of sulphoacetic acid is added to 24.5 g of the intermediate thus obtained, and the mixture is heated at 80°–100° C. for 7 hours until the evolution of gas has ceased.

A brown, water-dispersible product is thus obtained, Thioether index 0.92 meq/g.

EXAMPLE 21

Preparation of a mixture of compounds of the formula I in which $R_1$ and $R_2$ denote the radical $C_{12}H_{25}$, X denotes the group

Y denotes the group

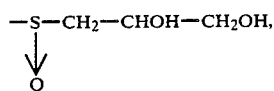

m=2 and n=12.

(a) Preparation of a mixture of polychlorinated intermediates 0.4 ml of $SnCl_4$ is added to 4.65 g (0.025 mol) of dodecan-1-ol (sold under the trademark "Alfol 12"), and a mixture containing 13.4 g (0.05 mol) of dodecyl glycidyl thioether and 27.6 g (0.3 mol) of epichlorohydrin is then added in the space of 1 and a half hours at a temperature of 80°–100° C. During this addition, 1.1 ml of $SnCl_4$ are added in portions.

The temperature is kept at 80°–100° C. for 4 hours after the addition.

The volatile compounds are removed by molecular distillation.

(b) Preparation of the mixture of non-ionic compounds 30 ml of ethanol and 9.7 g (0.082 mol) of thioglycerol, and then 8.3 g of an aqueous solution of NaOH containing 9.9 meq/g, are added to 16 g (82 meq/g of chlorine) of the intermediate thus obtained, and the mixture is heated for 4 hours at 70°–80° C.

The solvents are evaporated off by distillation under reduced pressure.

A pasty, brown, water-dispersible mixture is thus obtained.

12 ml of water are added to 24 g (90 meq/g of thioether) of the above product, and 8 ml of hydrogen peroxide of 200 volumes strength (60% by weight) are then added at 35°–40° C. in the course of about 1 hour 30 minutes.

After one night at ambient temperature, virtually all the hydrogen peroxide has reacted.

A product which is orange-yellow in colour and which is soluble in water with slight turbidity and contains about 67% of active ingredient is thus obtained.

EXAMPLE 22

Preparation of a mixture of non-ionic oligomers of the general formula (I) in which $R_1$ and $R_2$ denote the radical —$C_{12}H_{25}$, X denotes the group —S→O, Y denotes the group —OH, m=2 and n=12.

0.03 ml of acetic acid is added to 5 g (4.6 meq of thioether groups) of the compounds obtained in accordance with Example 20, and 0.26 ml of hydrogen peroxide of 200 volumes strength (60% strength by weight) is then added at 35° C.

A brown product is obtained which dissolves in water to give a slight turbidity, which does not intensify on heating.

EXAMPLE 23

Preparation of a mixture of cationic oligomers of the general formula (I) in which: $R_1$ denotes the radical —$C_{16}H_{33}$, $R_2$ denotes the radical —$C_{12}H_{25}$, X denotes the group —$CH_2$—, Y denotes the group

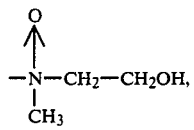

m=4 and n=20, which oligomers are crosslinked with the bis-glycidyl ether of bisphenol A, p being equal to 0.7.

0.05 ml of acetic acid is added to 10 g (43.5 meq of basic groups) of the compounds prepared in accordance with Example 14, and 2.5 ml of hydrogen peroxide of 200 volumes strength (60% strength by weight) are added dropwise at 45° C.

Thickening and decoloration of the reaction mixture are observed and this mixture is finally in the form of a perfectly water-soluble paste which is pale yellow in colour.

The cloud point in 25% by weight aqueous sodium chloride solution is above 100° C.

EXAMPLE 24

Preparation of a mixture of quaternary oligomers of the general formula (I) in which: $R_1$ denotes the radical —$C_{16}H_{33}$, $R_2$ denotes the radical —$C_{12}H_{25}$, X denotes the group, —$CH_2$—, Y denotes the group

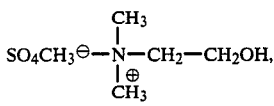

m=4 and n=20, which oligomers are crosslinked with the bis-glycidyl ether of bisphenol A, p being equal to 0.7.

5 ml of methanol are added to 10 g (43.5 meq of basic groups) of the compounds obtained in accordance with Example 14, and 5.5 g (0.043 mol) of dimethyl sulphate are then added at a temperature of 35° C.

After stirring for 3 hours, the methanol is removed under reduced pressure and a translucent, rose-coloured, perfectly water-soluble mixture is thus obtained.

Basicity index 0.

EXAMPLE 25

Preparation of a mixture of zwitterionic oligomers of the general formula (I) in which: $R_1$ denotes the radical —$C_{16}H_{33}$, $R_2$ denotes the radical —$C_{12}H_{25}$, X denotes the group —$CH_2$—, Y denotes the group

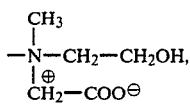

m=4 and n=20, which oligomers are crosslinked with the bis-glycidyl ether of bisphenol A, p being equal to 0.7.

15 g of a 35% strength aqueous solution of sodium monochloroacetate are added to 10 g (43.5 meq of basic groups) of the compounds obtained in accordance with Example 14, solubilised in 10 g of water.

After heating for 5 hours at 70° C., a degree of conversion of 91% is achieved.

The resulting solution remains perfectly limpid after dilution with water.

Ionised chlorine index 1.13 meq/g.

EXAMPLE 26

Preparation of a mixture of non-ionic oligomers of the general formula (I) in which: $R_1$ denotes the radical —$C_{12}H_{25}$, $R_2$ denotes the radical —$C_{12}H_{25}$, X denotes the group —$CH_2$—, Y denotes the group —OH, m=2 and n=9.

0.4 ml of $BF_3$/ether complex is added to 37.2 g (0.2 mol) of dodecan-1-ol sold under the registered trademark "Alfol 12", and 96 g (0.4 mol) of 1,2-epoxyhexadecane and 166.5 g (1.8 mols) of epichlorohydrin are then added at 50° C.; during the addition of the epoxide mixture, 2 times 0.3 ml of $BF_3$ complex are added.

After the virtually total conversion of the epoxide groups, the reaction mixture is taken up in 300 g of dipropylene glycol, 185 g (1.89 mols) of potassium acetate are added and the mixture is then heated for 6 hours at 180° C.

190 g of a 40% strength solution of sodium hydroxide (1.9 mols) are then added at 90° C. After stirring for 1 hour, the mixture is washed three times with 500 ml of boiling water in the presence of primary butanol in order to facilitate decantation. The product is dried under reduced pressure; it is in the form of a thick, brown, water-dispersible oil.

Hydroxyl number: 7.3 meq/g.

Cloud point in butyldiglycol: 79° C.

EXAMPLE 27

Preparation of a mixture of anionic oligomers of the general formula (I) in which: $R_1$ denotes the radical —$C_{12}H_{25}$, $R_2$ denotes the radical —$C_{12}H_{25}$, X denotes the group —$CH_2$—, Y denotes the group

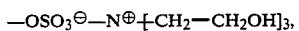

m=2 and n=9.

20 ml of chloroform are added to 20 g (147 meq of hydroxyl groups) of the compounds obtained in accordance with Example 26, and 17 g of chlorosulphonic acid, solubilised in 10 ml of chloroform, are then added at 30° C. in the space of 1 hour.

After stirring for 1 hour at 30° C., the chloroform is removed under reduced pressure. The reaction mixture is taken up in 20 ml of tert.-butyl alcohol and the resulting mixture is then neutralised with 22.6 g (0.15 mol) of triethanolamine, solubilised in 20 g of tert.-butyl alcohol.

After removing the solvent, a thick, brown, water-soluble oil is obtained.

The cloud point in 25% by weight aqueous sodium chloride solution is above 100° C.

EXAMPLE 28

Preparation of a mixture of non-ionic oligomers of the general formula (I) in which: $R_1$ denotes the radical —$C_{12}H_{25}$, $R_2$ denotes the radical —$C_8H_{17}$, X denotes the group —$CH_2$—, Y denotes the group —OH, m=3 and n=10.

0.42 ml of $BF_3$ etherate is added to 18.6 g (0.1 mol) of dodecan-1-ol sold under the registered trademark "Alfol 12", and 55 g (0.3 mol) of 1,2-epoxydodecane, mixed with 92.5 g (1 mol) of epichlorohydrin, are then added dropwise at 50° C. A further 0.45 ml of $BF_3$ etherate is added in portions, whilst stirring.

160 g of butyldiglycol and 100 g of potassium acetate are added to 162 g (976 meq of organic chlorine) of the derivative thus obtained.

The reaction mixture is then heated for 5 hours at 180° C. 110 g of a 40% strength solution of sodium hydroxide are then added at ambient temperature. After stirring for 1 hour, the excess sodium hydroxide is neutralised with hydrochloric acid, and 250 ml of water are added in order to solubilise the electrolytes present.

The organic phase is decanted and the solvent is removed under reduced pressure.

A thick, brown, water-dispersible oil is thus obtained.

The cloud point of 5% by weight of product in a 28.5% aqueous butyldiglycol solution is 70° C.

EXAMPLE 29

Preparation of a mixture of non-ionic oligomers of the general formula (I) in which: $R_1$ denotes a hydrocarbon radical derived from alcohols of lanoline, X denotes the group —O—, $R_2$ denotes $C_{16}H_{33}$, Y denotes the group

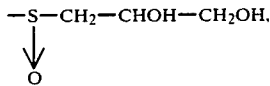

m=3 and n=20.

1.2 ml of tin tetrachloride are added to 20.8 g (50 meq of hydroxyl groups) of lanoline alcohols, and 44.7 g (0.15 mol) of hexadecyl glycidyl ether, mixed with 92.5 g (1 mol) of epichlorohydrin, are then added at 100° C.

During the addition, a further 1 ml of tin tetrachloride is added. Heating is maintained until the epoxide groups have disappeared. The product thus obtained is taken up in 70 ml of absolute ethanol and the mixture is heated to 80° C. At this temperature, 108 g (1 mol) of thioglycerol are added and 100 g of a 40% strength solution of sodium hydroxide are then added dropwise.

The reaction mixture is heated until the mercaptan groups have virtually completely disappeared.

The reaction mixture is taken up in 150 ml of butanol and 500 ml of boiling water. After separating off the aqueous phase, the solvents are removed under reduced pressure.

A pale brown, very water-dispersible paste is thus obtained which has a hard consistency.

50 g (215 meq of thioether groups) of the product thus obtained are diluted with 30 ml of water. 18 ml of hydrogen peroxide of 130 volumes strength are then added, whilst stirring vigorously.

A pale yellow, aqueous solution is thus obtained which is limpid on dilution.

The cloud point in a 25% by weight aqueous sodium chloride solution is above 100° C.

EXAMPLE 30

A fluid emulsion of the oil-in-water type is prepared by mixing 10 parts of compounds according to Example 26, 40 parts of petroleum jelly, 50 parts of water and 0.1 part of perfume.

This gives an emulsion which can be used as a beauty milk.

EXAMPLE 31

This example demonstrates the ability of the surface-active statistical oligomers of the formula (I) to disperse hydrocarbons.

The oligomer chosen is that which is most suitable for the hydrocarbon to be dispersed or emulsified.

This determination can be made by means of the test below.

150 ml of water are introduced into a 150 ml beaker. 5 g of dodec-1-ene, in which 0.5 g of a statistical oligomer of the formula (I) has been incorporated beforehand, are deposited on the surface. The mixture is stirred by means of a magnetic stirrer for 1 minute at 20° C.

After the stirring has stopped, the time after which the hydrocarbon begins to separate out distinctly from the aqueous phase is measured. In order to facilitate the observation, a dyestuff, for example the dyestuff orange OT, is dissolved in the hydrocarbon in a proportion of 0.05%, relative to the weight of the hydrocarbon.

Table I shows the stability of the dispersions obtained with a few oligomers prepared in the above examples.

TABLE I

| Stability of the dodec-1-ene dispersions in seconds for various statistical oligomers of the formula (I) | |
|---|---|
| Oligomer prepared in accordance with Example No. | Stability (in seconds) |
| 1 | 300 |
| 2 | 1,800 |
| 5 | 300 |
| 6 | 1,200 |
| 20 | 300 |
| 22 | 200 |
| 28 | 1,800 |

The dispersing power of the statistical oligomers of the formula (I) according to the present application was compared with the dispersing power of the closest block oligomers.

Table II gives, by way of comparison, the dispersing power of a few block oligomers described, respectively, in French Applications No. 76/21,961 of July 19, 1976, published under No. 2,401,187, and No. 76/21,962 of July 19, 1976, published under No. 2,359,165, of the Applicant Company.

TABLE II

| Stability of the dodec-1-ene dispersions in seconds with block oligomers. | | | |
|---|---|---|---|
| Block oligomers | Example No. | French Application No. | Stability in seconds |
| A | Ib | 2,401,187 | 20 |
| B | Ic | " | 20 |
| C | Ib | 2,359,165 | 60 |
| D | IIc | " | 90 |
| E | IId | " | 90 |

The formulae of the block oligomers A, B, C, D and E are given below:

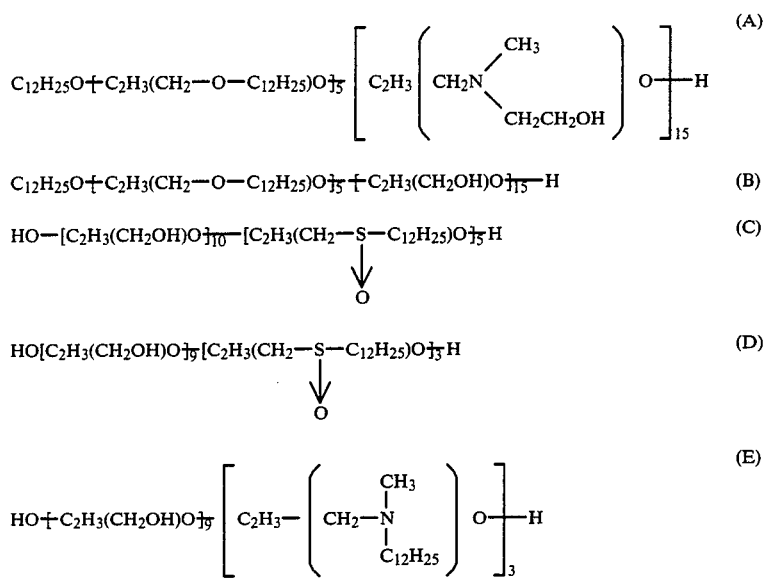

$$C_{12}H_{25}O\text{+}[C_2H_3(CH_2-O-C_{12}H_{25})O]_{15}\text{+}C_2H_3(CH_2OH)O]_{15}\text{-}H \quad (B)$$

(C)

(D)

(E)

It is found that the statistical oligomers according to the present application make it possible to obtain, using hydrocarbons, a dispersion or emulsion which is sufficiently stable to be used for cleaning containers which have contained hydrocarbons, and that the closest block oligomers of the state of the art produce dispersions which are insufficiently stable to permit the use of these block oligomers for dispersing hydrocarbons.

We claim:

1. A surface-active statistical oligomer of the average formula $$R_1O\text{+}[C_2H_3(CH_2-X-R_2)O]_m[C_2H_3(CH_2-Y)O]_n\text{+}H \quad (I)$$

in which $R_1$ denotes an unsubstituted or substituted, aliphatic or cycloaliphatic radical having from 4 to 30 carbon atoms, $R_2$ denotes a linear or branched alkyl radical having from 5 to 20 carbon atoms, m and n, which are identical or different, denote a number from 1 to 25, X denotes $CH_2$, O or $$\underset{(O)_u}{\overset{\downarrow}{S,}}$$

in which u denotes 0 or 1, and Y denotes one of the groups:

—OH (a)

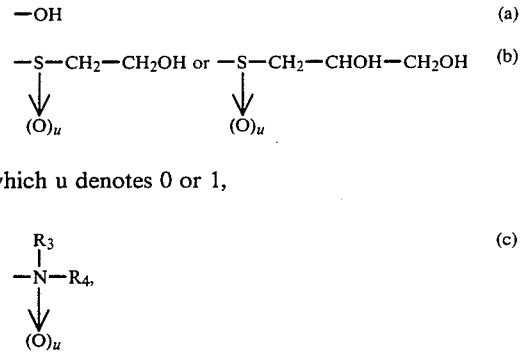

in which u denotes 0 or 1,

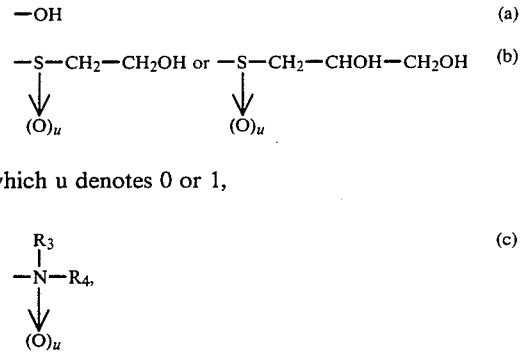

in which u denotes 0 or 1 and $R_3$ and $R_4$ which are identical or different, denote an alkyl or hydroxyalkyl radical containing from 1 to 3 carbon atoms, or $R_3$ and $R_4$ form, together with the nitrogen atom to which they are attached, a heterocyclic ring having 5 or 6 ring members

in which HV denotes an inorganic or organic acid and u, $R_3$ and $R_4$ are as defined in (c),

in which $R_5$ denotes a methyl, ethyl or hydroxyethyl radical, Z denotes an anion, and $R_3$ and $R_4$ are as defined in (c),

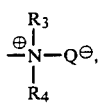 (f)

in which $Q^{\ominus}$ denotes an anion and $R_3$ and $R_4$ are as defined in (c), (g) —OSO₃M, in which M denotes a hydrogen atom or an alkali metal or alkaline earth metal, (h) —OCOCH₂SO₃M, in which M denotes a hydrogen atom or an alkali metal or alkaline earth metal, or

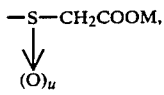

in which u denotes 0 or 1 and M denotes a hydrogen atom or an alkali metal or alkaline earth metal.

2. An oligomer according to claim 1, in which X denotes O or CH₂.

3. An oligomer according to claim 1, in which Y denotes OH.

4. A surface-active statistical oligomer of the average formula (I)

$$R_1O+[C_2H_3(CH_2XR_2)O]_m[C_2H_3(CH_2Y)O]_n+H \quad (I)$$

which has been crosslinked by a diepoxide, the molar amount of the diepoxide being less than or equal to 5 mol percent based on the molar amounts of the units —[C₂H₃(CH₂XR₂)O]— and —[C₂H₃(CH₂Y)O]—, $R_1$, $R_2$, X and Y being as defined in claim 1.

5. A crosslinked oligomer according to claim 4 in which the diepoxide is diepoxybutane, bis-epoxypropyl-piperazine, diglycidyl ether or the bis-glycidyl ether of bisphenol A.

6. An oligomer according to claim 1, in which m denotes a number from 1 to 15 and n, which is equal to or greater than m, denotes a number from 1 to 25.

7. An oligomer according to claim 1, in which $R_1$ denotes an alkyl or alkenyl radical having from 8 to 18 carbon atoms.

8. An oligomer according to claim 1, in which $R_2$ denotes a linear or branched alkyl radical having from 7 to 16 carbon atoms.

9. An oligomer according to claim 1, in which R denotes an alkyl radical having from 12 to 16 carbon atoms or a hydrocarbon radical derived from lanoline alcohols.

10. An oligomer according to claim 1, in which m denotes a number from 2 to 10 and n, which is equal to or greater than m, denotes a number from 3 to 20.

11. A surface-active statistical oligomer of the average formula $$R_1O+[C_2H_3(CH_2-X-R_2)O]_m[C_2H_3(CH_2-Y)O]_n+H$$

wherein
$R_1$ is selected from the group consisting of 2-ethyl hexyl, —C₁₂H₂₅, a mixture of —C₁₂H₂₅ and —C₁₄H₂₉, —C₁₆H₃₃ and the hydrocarbon residue of lanolin,
$R_2$ is selected from the group consisting of a mixture of —C₇H₁₅ to —C₁₀H₂₁, —C₈H₁₇, 2-ethyl hexyl, —C₁₂H₂₅ and —C₁₆H₃₃, X is selected from the group consisting of —O—, —CH₂—, —S— and

Y is selected from the group consisting of

—OH, (a)

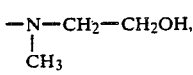 (b)

—S—CH₂—COOH, (c)

—OCO—CH₂—SO₃H, (d)

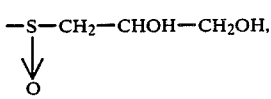 (e)

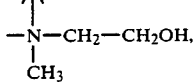 (f)

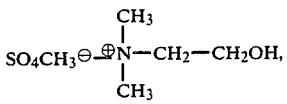 (g)

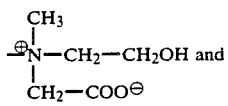 (h)

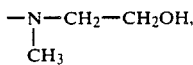 (i)

m and n each independently represent an integer or decimal number from 1 to 25.

12. A surface-active statistical oligomer of claim 11 selected from the group consisting of (1) an oligomer wherein $R_1$ is —C₁₂H₂₅, $R_2$ is C₁₂H₂₅, X is —O—, Y is

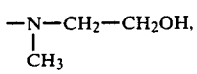

m is 5 and n is 15;

(2) an oligomer wherein $R_1$ is C₁₂H₂₅, $R_2$ is C₁₂H₂₅, X is —O—, Y is OH, m is 5 and n is 15;

(3) an oligomer wherein $R_1$ is C₁₂H₂₅, $R_2$ is C₁₂H₂₅, X is —O—, Y is

—N—CH₂—CH₂OH,
|
CH₃ m is 5 and n is 15, said oligomer being crosslinked with bis-glycidyl ether of bisphenol A;

(4) an oligomer wherein $R_1$ is C₁₂H₂₅, $R_2$ is C₈H₁₇, X is —CH₂—, Y is OH, m is 4 and n is 15;

(5) an oligomer wherein $R_1$ is C₁₂H₂₅, $R_2$ is C₈H₁₇, X is —CH₂—, Y is

—N—CH$_2$—CH$_2$OH,
|
CH$_3$ m is 5 and n is 15;

(6) an oligomer wherein R$_1$ is C$_{12}$H$_{25}$, R$_2$ is C$_8$H$_{17}$, X is —CH$_2$—, Y is OH, m is 5 and n is 15;

(7) an oligomer wherein R$_1$ is C$_{12}$H$_{25}$, R$_2$ is C$_8$H$_{17}$, X is —CH$_2$—, Y is

—N—CH$_2$—CH$_2$OH,
|
CH$_3$ m is 5 and n is 15, said oligomer being crosslinked with bis-glycidyl ether of bisphenol A;

(8) an oligomer wherein R$_1$ is C$_{12}$H$_{25}$, R$_2$ is C$_8$H$_{17}$, X is —CH$_2$—, Y is OH, m is 5 and n is 15, said oligomer being crosslinked with bis-glycidyl ether of bisphenol A;

(9) an oligomer wherein R$_1$ is C$_{12}$H$_{25}$, R$_2$ is C$_8$H$_{17}$, X is —CH$_2$—, Y is

—N—CH$_2$—CH$_2$OH,
|
CH$_3$ m is 5 and n is 15, said oligomer being crosslinked with bis-glycidyl ether of bisphenol A;

(10) an oligomer wherein R$_1$ is C$_{12}$H$_{25}$, R$_2$ is C$_8$H$_{17}$, X is —CH$_2$—, Y is

—N—CH$_2$—CH$_2$OH,
|
CH$_3$ m is 10 and n is 15;

(11) an oligomer wherein R$_1$ is C$_{12}$H$_{25}$, R$_2$ is C$_8$H$_{17}$, X is —CH$_2$—, Y is OH, m is 10 and n is 5;

(12) an oligomer wherein R$_1$ is a mixture of C$_{12}$H$_{25}$ and C$_{14}$H$_{29}$, R$_2$ is a mixture of C$_7$H$_{15}$ to C$_{10}$H$_{21}$, X is —CH$_2$—, Y is OH, m is 5 and n is 15;

(13) an oligomer wherein R$_1$ is C$_{16}$H$_{33}$, R$_2$ is C$_{12}$H$_{25}$, X is —CH$_2$—, Y is

—N—CH$_2$—CH$_2$OH,
|
CH$_3$ m is 4 and n is 20, said oligomer being crosslinked with bis-glycidyl ether of bisphenol A;

(14) an oligomer wherein R$_1$ is C$_{16}$H$_{33}$, R$_2$ is C$_{12}$H$_{25}$, X is —CH$_2$—, Y is OH, m is 4 and n is 20, said oligomer being crosslinked with bis-glycidyl ether of bisphenol A;

(15) an oligomer wherein R$_1$ is C$_{16}$H$_{33}$, R$_2$ is C$_{12}$H$_{25}$, X is —CH$_2$—, Y is —S—CH$_2$—COOH, m is 4 and n is 20, said oligomer being crosslinked with bis-glycidyl ether of bisphenol A;

(16) an oligomer wherein R$_1$ is 2-ethyl hexyl, R$_2$ is 2-ethyl hexyl, X is O, Y is OH, m is 6 and n is 20;

(17) an oligomer wherein R$_1$ is 2-ethyl hexyl, R$_2$ is 2-ethyl hexyl, X is O, Y is OH, m is 2 and n is 8;

(18) an oligomer wherein R$_1$ is CH$_{12}$H$_{25}$, R$_2$ is C$_{12}$H$_{25}$, X is S, Y is —OCO—CH$_2$—SO$_3$H, m is 3 and n is 3,

(19) an oligomer wherein R$_1$ is C$_{12}$H$_{25}$, R$_2$ is C$_{12}$H$_{25}$, X is S, Y is OH, m is 2 and n is 12;

(20) an oligomer wherein R$_1$ is C$_{12}$H$_{25}$, R$_2$ is C$_{12}$H$_{25}$, X is

—S—,
↓
O

Y is

—S—CH$_2$—CHOH—CH$_2$OH,
↓
O m is 2 and n is 12;

(21) an oligomer wherein R$_1$ is C$_{12}$H$_{25}$, R$_2$ is C$_{12}$H$_{25}$, X is

—S—,
↓
O

Y is OH, m is 2 and n is 12;

(22) an oligomer wherein R$_1$ is C$_{16}$H$_{33}$, R$_2$ is C$_{12}$H$_{25}$, X is —CH$_2$—, Y is

O
↑
—N—CH$_2$—CH$_2$OH,
|
CH$_3$ m is 4 and n is 20, said oligomer being crosslinked with bis-glycidyl ether of bisphenol A;

(23) an oligomer wherein R$_1$ is C$_{16}$H$_{33}$, R$_2$ is C$_{12}$H$_{25}$, X is —CH$_2$—, Y is

CH$_3$
|
SO$_4$CH$_3$⊖—N⊕—CH$_2$—CH$_2$OH,
|
CH$_3$ m is 4 and n is 20, said oligomer being crosslinked with bis-glycidyl ether of bisphenol A;

(24) an oligomer wherein R$_1$ is C$_{16}$H$_{33}$, R$_2$ is C$_{12}$H$_{25}$, X is —CH$_2$—, Y is

CH$_3$
|
—N⊕—CH$_2$—CH$_2$OH,
|
CH$_2$—COO⊖ m is 4 and n is 20, said oligomer being crosslinked with bis-glycidyl ether of bisphenol A;

(25) an oligomer wherein R$_1$ is C$_{12}$H$_{25}$, R$_2$ is C$_{12}$H$_{25}$, X is —CH$_2$—, Y is OH, m is 2 and is 9;

(26) an oligomer wherein R$_1$ is C$_{12}$H$_{25}$, R$_2$ is C$_{12}$H$_{25}$, X is —CH$_2$—, Y is

—OSO$_3$⊖—N⊕─[CH$_2$—CH$_2$OH]$_3$, m is 2 and n is 9;

(27) an oligomer wherein $R_1$ is $C_{12}H_{25}$, $R_2$ is $C_8H_{17}$, X is —$CH_2$—, Y is OH, m is 3 and n is 10; and
(28) an oligomer wherein $R_1$ is the hydrocarbon residue of lanolin, $R_2$ is $C_{16}H_{33}$, X is 0, Y is

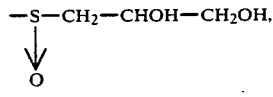

m is 3 and n is 20.

13. A surface-active statistical oligomer of the average formula $$R_1O\mathrm{+}[C_2H_3(CH_2-X-R_2)O]_m[C_2H_3(CH_2-Y)O]_n\mathrm{+}H \quad (I)$$

wherein
  $R_1$ represents an unsubstituted or substituted, aliphatic or cycloaliphatic radical having from 4 to 30 carbon atoms,
  $R_2$ represents linear or branched alkyl having from 5 to 20 carbon atoms,
  m and n each independently represent an integer or decimal number from 1 to 25,
  X represents $CH_2$, O or

wherein u is 0 or 1, and
  Y represents OH.

14. The surface-active statistical oligomer of claim 13 selected from the group consisting of
  (1) an oligomer wherein $R_1$ is $C_{12}H_{25}$, $R_2$ is $C_{12}H_{25}$, X is —O—, Y is OH, m is 5 and n is 15;
  (2) an oligomer wherein $R_1$ is $CH_{12}H_{25}$, $R_2$ is $C_8H_{17}$, X is —$CH_2$—, Y is OH, m is 4 and n is 15;
  (3) an oligomer wherein $R_1$ is $C_{12}H_{25}$, $R_2$ is $C_8H_{17}$, X is —$CH_2$—, Y is OH, m is 5 and n is 15;
  (4) an oligomer wherein $R_1$ is $C_{12}H_{25}$, $R_2$ is $C_8H_{17}$, X is —$CH_2$—, Y is OH, m is 10 and n is 5;
  (5) an oligomer wherein $R_1$ is a mixture of $C_{12}H_{25}$ and $C_{14}H_{29}$, $R_2$ is a mixture of $C_7H_{15}$ to $C_{10}H_{21}$, X is —$CH_2$—, Y is OH, m is 5 and n is 15;
  (6) an oligomer wherein $R_1$ is 2-ethyl hexyl, $R_2$ is 2-ethyl hexyl, X is 0, Y is OH, m is 6 and n is 20;
  (7) an oligomer wherein $R_1$ is 2-ethyl hexyl, $R_2$ is 2-ethyl hexyl, X is 0, Y is OH, m is 2 and n is 8;
  (8) an oligomer wherein $R_1$ is $C_{12}H_{25}$, $R_2$ is $C_{12}H_{25}$, X is S, Y is OH, m is 2 and n is 12;
  (9) an oligomer wherein $R_1$ is $C_{12}H_{25}$, $R_2$ is $C_{12}H_{25}$, X is $$\begin{array}{c} S. \\ \downarrow \\ O \end{array}$$

Y is OH, m is 2 and n is 12;
  (10) an oligomer wherein $R_1$ is $C_{12}H_{25}$, $R_2$ is $C_{12}H_{25}$, X is —$CH_2$—, Y is OH, m is 2 and n is 9; and
  (11) an oligomer wherein $R_1$ is $C_{12}H_{25}$, $R_2$ is $C_8H_{17}$, X is —$CH_2$—, Y is OH, m is 3 and n is 10.

15. The surface-active statistical oligomer of claim 13 wherein $R_1$ is $C_{12}H_{25}$, $R_2$ is $C_8H_{17}$, X is —$CH_2$—, Y is OH, m is 5 and n is 15.

16. A cosmetic composition for the care of the skin, nails and hair comprising in a cosmetic carrier 0.0005 to 80 percent by weight relative to the total weight of the composition of a surface active statistical oligomer of the average formula $$R_1O\mathrm{+}[C_2H_3(CH_2-X-R_2)O]_m[C_2H_3(CH_2-Y)O]_n\mathrm{+}H$$

wherein
  $R_1$ represents an unsubstituted or substituted aliphatic or cycloaliphatic radical having from 4 to 30 carbon atoms,
  $R_2$ represents a linear or branched alkyl radical having from 5 to 20 carbon atoms,
  m and n each independently represent a number from 1 to 25,
  X represents $CH_2$, O or $$\begin{array}{c} S \\ \downarrow \\ (O)_u \end{array}$$

wherein u is 0 or 1, and
  Y is selected from the group consisting of

—OH  (a)

wherein u is 0 or 1, $$\begin{array}{c} R_3 \\ | \\ -N-R_4 \\ \downarrow \\ (O)_u \end{array} \quad (c)$$

wherein u is 0 or 1 and $R_3$ and $R_4$ each independently represent alkyl or hydroxyalkyl containing 1-3 carbon atoms, or $R_3$ and $R_4$ form, together with the nitrogen atom to which they are attached, a heterocyclic ring having 5 or 6 ring members, $$\begin{array}{c} R_3 \\ | \\ -N-R_4.HV, \\ \downarrow \\ (O)_u \end{array} \quad (d)$$

wherein HV represents an inorganic or organic acid and u, $R_3$ and $R_4$ are as defined in (c), $$\begin{array}{c} R_3 \\ | \\ -N-R_5\ Z^\ominus, \\ \oplus | \\ R_4 \end{array} \quad (e)$$

wherein $R_5$ represents methyl, ethyl or hydroxyethyl, Z represents an anion and $R_3$ and $R_4$ are as defined in (c),

 (f)

wherein $Q^\ominus$ represents an anion and $R_3$ and $R_4$ are as defined in (c), (g) —OSO$_3$M, wherein M represents hydrogen, an alkali metal or an alkaline earth metal, (h) —OCOCH$_2$SO$_3$M, wherein M represents hydrogen, an alkali metal or an alkaline earth metal, or

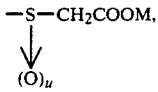

wherein u is 0 or 1 and M represents hydrogen, an alkali metal or an alkaline earth metal.

17. The cosmetic composition of claim 16 in the form of a solution, an aqueous or aqueous-alcoholic dispersion, a cream, a gel, an emulsion or an aerosol.

18. The cosmetic composition of claim 16 which also includes an effective amount of at least one cosmetic adjuvant selected from an acid, a base, a foam synergistic agent, a foam stabilizer, a thickener, an opacifier, a sequestering agent, a super fatting agent, an antiseptic, a preservative, a treating product, a polymer, a pigment, a dyestuff, a solvent for a dyestuff, a sun filter or an oxidizing agent.

19. A cosmetic composition for the care of the skin, nails and hair comprising in a cosmetic carrier 0.0005 to 80 percent by weight relative to the total weight of the composition of a surface active statistical oligomer of the average formula

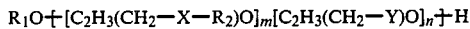

wherein
$R_1$ represents an unsubstituted or substituted, aliphatic or cycloaliphatic radical having from 4 to 30 carbon atoms,
$R_2$ represents linear or branched alkyl having from 5 to 20 carbon atoms, m and n each independently represent an integer or decimal number from 1 to 25,
X represents CH$_2$, O or

wherein u is 0 or 1, and
Y represents OH.

20. The cosmetic composition of claim 19 where the surface active statistical oligomer is one wherein $R_1$ is $C_{12}H_{25}$, $R_2$ is $C_8H_{17}$, X is —CH$_2$—, Y is OH, m is 5 and n is 15.

21. The cosmetic composition of claim 19 wherein the surface-active statistical oligomer is selected from the group consisting of
(1) an oligomer wherein $R_1$ is $C_{12}H_{25}$, $R_2$ is $C_{12}H_{25}$, X is —O—, Y is OH, m is 5 and n is 15;
(2) an oligomer wherein $R_1$ is $C_{12}H_{25}$, $R_2$ is $C_8H_{17}$, X is —CH$_2$—, Y is OH, m is 4 and n is 15;
(3) an oligomer wherein $R_1$ is $C_{12}H_{25}$, $R_2$ is $C_8H_{17}$, X is —CH$_2$—, Y is OH, m is 5 and n is 15;
(4) an oligomer wherein $R_1$ is $C_{12}H_{25}$, $R_2$ is $C_8H_{17}$, X is —CH$_2$—, Y is OH, m is 10 and n is 5;
(5) an oligomer wherein $R_1$ is a mixture of $C_{12}H_{25}$ and $C_{14}H_{29}$, $R_2$ is a mixture of $C_7H_{15}$ to $C_{10}H_{21}$, X is —CH$_2$—, Y is OH, m is 5 and n is 15;
(6) an oligomer wherein $R_1$ is 2-ethyl hexyl, $R_2$ is 2-ethyl hexyl, X is O, Y is OH, m is 6 and n is 20;
(7) an oligomer wherein $R_1$ is 2-ethyl hexyl, $R_2$ is 2-ethyl hexyl, X is O, Y is OH, m is 2 and n is 8;
(8) an oligomer wherein $R_1$ is $C_{12}H_{25}$, $R_2$ is $C_{12}H_{25}$, X is S, Y is OH, m is 2 and n is 12;
(9) an oligomer wherein $R_1$ is $C_{12}H_{25}$, $R_2$ is $C_{12}H_{25}$, X is

Y is OH, m is 2 and n is 12;
(10) an oligomer wherein $R_1$ is $C_{12}H_{25}$, $R_2$ is $C_{12}H_{25}$, X is —CH$_2$—, Y is OH, m is 2 and n is 9; and
(11) an oligomer wherein $R_1$ is $C_{12}H_{25}$, $R_2$ is $C_8H_{17}$, X is —CH$_2$—, Y is OH, m is 3 and n is 10.

* * * * *